United States Patent [19]

Brown et al.

[11] Patent Number: 5,782,814
[45] Date of Patent: Jul. 21, 1998

[54] APPARATUS FOR DETERMINING AND RECORDING INJECTION DOSES IN SYRINGES USING ELECTRICAL INDUCTANCE

[75] Inventors: Stephen J. Brown, Mountain View, Calif.; Erik K. Jensen, Stockton, N.J.

[73] Assignee: Raya Systems, Inc., Mountain View, Calif.

[21] Appl. No.: 681,290

[22] Filed: Jul. 22, 1996

Related U.S. Application Data

[63] Continuation-in-part of Ser. No. 278,929, Jul. 22, 1994, Pat. No. 5,569,212.
[51] Int. Cl.⁶ .................................................. A61M 5/00
[52] U.S. Cl. ........................ 604/207; 604/246; 235/449; 222/23; 222/30
[58] Field of Search ...................... 604/207–211, 246, 604/407; 128/DIG. 1; 235/449–450; 222/23, 30

[56] References Cited

U.S. PATENT DOCUMENTS

| | | |
|---|---|---|
| 4,846,797 | 7/1989 | Howson et al. . |
| 4,853,521 | 8/1989 | Claeys et al. . |
| 4,950,246 | 8/1990 | Muller . |
| 4,978,335 | 12/1990 | Arthur, III . |
| 5,019,974 | 5/1991 | Beckers . |
| 5,176,502 | 1/1993 | Sanderson et al. . |
| 5,569,212 | 10/1996 | Brown . |
| 5,593,390 | 1/1997 | Castellano et al. . |
| 5,628,309 | 5/1997 | Brown . |
| 5,651,775 | 7/1997 | Walker et al. . |

*Primary Examiner*—Mark Bockelman
*Attorney, Agent, or Firm*—Lumen Intellectual Property Services

[57] ABSTRACT

An apparatus for determining and recording a dose of an agent delivered with a syringe. The syringe has a barrel for holding the agent and a plunger movably positioned in the barrel for expelling the agent. The plunger includes a magnetically responsive element, such as an iron core. The apparatus has a receptacle for receiving the syringe for dose measurement. An inductive element is positioned coaxially to the receptacle to produce a magnetic field. When the syringe is placed in the receptacle, the intensity of the magnetic field varies in dependence upon the position of the plunger in the barrel. The magnetic field induces a voltage in a conducting loop. A voltage meter is connected to the conducting loop to measure the induced voltage. A microprocessor is connected to the voltage meter to calculate the dose from the measurement of the induced voltage. A recorder, such as a digital memory unit, records the dose.

32 Claims, 6 Drawing Sheets

APPARATUS FOR DETERMINING AND RECORDING INJECTION DOSES IN SYRINGES USING ELECTRICAL INDUCTANCE

CONTINUATION APPLICATION INFORMATION

This application is a continuation in part of application Ser. No. 08/278,929, filed Jul. 22, 1994, now U.S. Pat. No. 5,569,212. This application is also related to application Ser. No. 08/591,308, filed Jan. 25, 1996, now U.S. Pat. No. 5,628,309. All of the above applications are hereby incorporated by reference.

BACKGROUND

1. Field of the Invention

The present invention relates to the field of injection syringes, and in particular to an apparatus for determining and recording the dose of an agent delivered with an injection syringe using electrical inductance measurements.

2. Description of Prior Art

In recent years, the value of keeping electronic medical records in place of paper records has been widely recognized in the healthcare industry. The use of electronic medical records allows healthcare providers and patients to store, retrieve, and share medical information with considerably more ease and accuracy. The sharing of medical information is particularly important in treatment programs involving self-administration of insulin, human growth hormone, or other medications in which patients themselves perform the injections and keep records.

Typically, these injections are performed using disposable syringes. Unfortunately, no adequate apparatus exists that electrically measures and records dose information from a disposable syringe. As a result, the patient performing the injection is burdened with the task of injecting the dose and then manually recording the dose amount in a log book.

Because of the frequency of such injections, often several times a day for diabetics, it becomes difficult to keep accurate records. Indeed, studies have shown that a patient's own records and recollections are often incomplete and inaccurate. Additionally, a patient may intentionally cheat while making self-recorded entries in an attempt to create a log book that will please his or her doctor. In the long-term, this makes patient monitoring extremely difficult and jeopardizes the treatment program, possibly even endangering the patient's life.

Attempts have been made at developing electronic management systems for assisting patients in self-administered drug programs. For example, U.S. Pat. No. 5,019,974 issued to Beckers describes a hand-held, microprocessor-based recorder that interfaces with a master computer. The patient enters therapy information into the recorder via a keyboard. The recorder includes a display for displaying treatment therapy guidelines to the patient. The recorder also has a blood glucose meter for recording the patient's blood glucose levels.

Unfortunately, the recorder described by Beckers does not automatically measure and record dose information from a disposable syringe. After injecting a dose, the patient must manually enter the dose information into the recorder using switches or keys. Although this is an improvement over keeping written records on paper, the effectiveness of the drug program is still limited by the patient's recollections and recordings, which are unreliable.

Attempts have also been made at developing devices that deliver a predetermined dose of medication and record the dose amount. For example, U.S. Pat. No. 5,176,502 issued to Sanderson et al. on Jan. 5, 1993 describes a syringe pump for expelling a preset dose of medication from a syringe. The syringe pump includes a syringe retainer for holding the syringe and a driver for engaging the plunger of the syringe. An electric motor pushes the driver and plunger into the syringe barrel to expel the medication.

The syringe pump further includes a monitoring circuit for monitoring the motion of the driver during the delivery of the medication. The monitoring circuit includes a linear potentiometer having an electrically conductive strip of resistive material. The resistive material is positioned such that it engages an electrical contact of the driver. The position of the electrical contact on the resistive strip varies the voltage of the monitoring circuit, thus indicating the position of the plunger inside the barrel. A microprocessor receives voltage signals from the monitoring circuit and compares the voltage signals to preprogrammed signals to determine if the plunger displacement corresponds to correct displacement for delivering the preset dose. A control mechanism connected to the microprocessor regulates the driver's movement to ensure the preset dose of medication is delivered.

Although the syringe pump described by Sanderson does allow electronic recording of dose information, it is only designed to deliver medication directly into an intravenous line. It is not designed to inject a patient directly nor can it measure and record a dose from a syringe unless the syringe pump pushes the plunger. Consequently, the syringe pump is of little use to an outpatient performing a self-injection treatment program.

Another device for injecting a preset dose of medication and for recording the injected dose is disclosed in U.S. Pat. No. 4,950,246 issued to Muller on Aug. 21, 1990. Muller describes a battery-operated injection pen having a pump rod driven by an electric motor. The electric motor is controlled by an electronic control unit that includes a microprocessor with a memory for storing dose information. The injection pen further includes a sensor connected to the control unit for electrically determining the position of the pump rod, and thus the amount of medication injected.

Although the injection pen described by Muller does electrically measure and record dose information, it has several disadvantages that preclude its widespread use. First, the injection pen is an expensive device requiring complicated electronic equipment to deliver and record doses. Second, because the injection pen integrates a syringe and electronic recorder into one device, it is not disposable. The patient must use it repeatedly for each injection, even after the injection pen has been contaminated with blood. Consequently, the injection pen does not provide an inexpensive, convenient, or hygienic solution to patients wishing to electrically measure and record injected dose information.

U.S. Pat. No. 4,853,521 issued to Ronald Claeys on Aug. 1, 1989 presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

While this apparatus comes closest to solving the problem, it involves many complicated steps of weighing syringes, scanning in bar codes, etc. These complex procedures as well as the high cost of the apparatus preclude effective home use. Additionally, the apparatus cannot be easily carried by the patient for recording doses while away from home. Thus, no inexpensive apparatus exists for electrically determining and recording dose information from a disposable syringe. Further, no such apparatus exists that is both simple in operation and easily carried by a patient.

OBJECTS AND ADVANTAGES OF THE INVENTION

In view of the above, it is an object of the present invention to provide an inexpensive apparatus for electrically determining and recording an injection dose delivered from a disposable syringe. It is another object of the invention to provide an apparatus that may be easily operated and carried by a user. A further object of the invention is to suit the apparatus to diabetic patients in particular.

These and other objects and advantages will become more apparent after consideration of the ensuing description and the accompanying drawings.

SUMMARY OF THE INVENTION

The invention presents an apparatus for determining and recording a dose of an agent delivered with a syringe. The syringe is of the type having a barrel for holding the agent and a plunger movably positioned in the barrel for expelling the agent. The plunger includes a magnetically responsive element selected from the group consisting of diamagnetic materials and paramagnetic materials.

In a first embodiment, an inductive element for generating a magnetic field is coupled to the barrel. The intensity of the magnetic field generated by the inductive element varies in dependence upon the position of the plunger inside the barrel. The position of the plunger inside the barrel also determines the volume of agent contained in the barrel, so that the dose may be determined by a measure of the generated magnetic field. The inductive element has a first terminal and a second terminal. An input terminal located on the outside of the syringe is electrically connected to the first terminal. An output terminal also located on the outside of the syringe is electrically connected to the second terminal.

The apparatus includes a housing having a placement field on its outer surface for placement of the syringe during dose measurement. The placement field has an input contact for contacting the input terminal and an output contact for contacting the output terminal. A voltage generator produces a voltage difference across the input contact and the output contact, thereby causing an electric current to flow through the inductive element when the input contact is contacting the input terminal and the output contact is contacting the output terminal.

The apparatus further includes a magnetic response measuring system located within the housing for measuring the magnetic field generated by the inductive element. In the first embodiment, the magnetic response measuring system includes a voltage meter connected to a conducting loop. The voltage meter measures a magnetically induced voltage in the conducting loop. A microprocessor is connected to the voltage meter to calculate the dose from the measured voltage. A recorder, such as a digital memory unit, records the calculated dose. The apparatus also includes an input/output port connected to the recorder so that recorded data may be transmitted through the input/output port to a host computer.

In a second embodiment of the invention, the apparatus includes an inductance meter connected to the input and output contacts to measure an inductance of the inductive element. Because the inductance of the inductive element also varies in dependence upon the position of the plunger inside the barrel, the dose may be determined by a measure of the inductance. As in the first embodiment, a microprocessor is connected to the inductance meter to calculate the dose from the measured inductance and record the dose in the recorder.

In a third embodiment of the invention, the inductive element is located in the apparatus rather than in the syringe. The housing has a receptacle for receiving the syringe and the inductive element is positioned coaxially to the receptacle. When the syringe is placed in the receptacle, the intensity of the magnetic field generated by the inductive element varies in dependence upon the position of the plunger inside the barrel. A voltage generator produces a voltage difference across the inductive element, thereby causing an electric current to flow through the inductive element. As in the first embodiment, a magnetic response measuring system measures the magnetic field generated by the inductive element. A microprocessor calculates the dose from the measurement, and a recorder records the calculated dose.

A fourth embodiment of the invention differs from the third embodiment in that the apparatus includes an inductance meter for measuring an inductance of the inductive element. As in the second embodiment, a microprocessor is connected to the inductance meter to calculate the dose from the measured inductance and record the dose in the recorder.

DESCRIPTION

Figure 1:
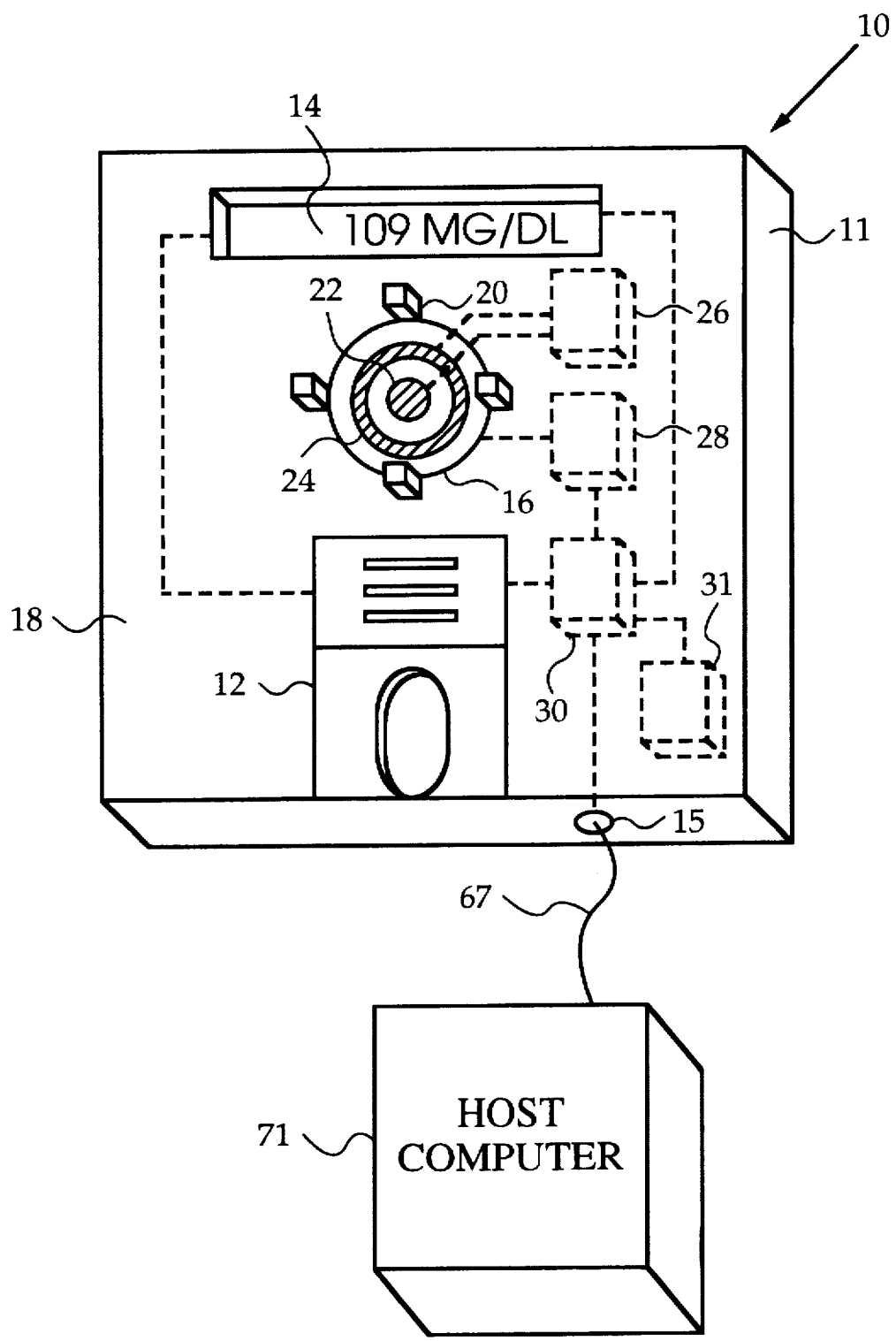
FIG. 1 is a three dimensional, schematic view of an apparatus according to the invention.
Figure 2:
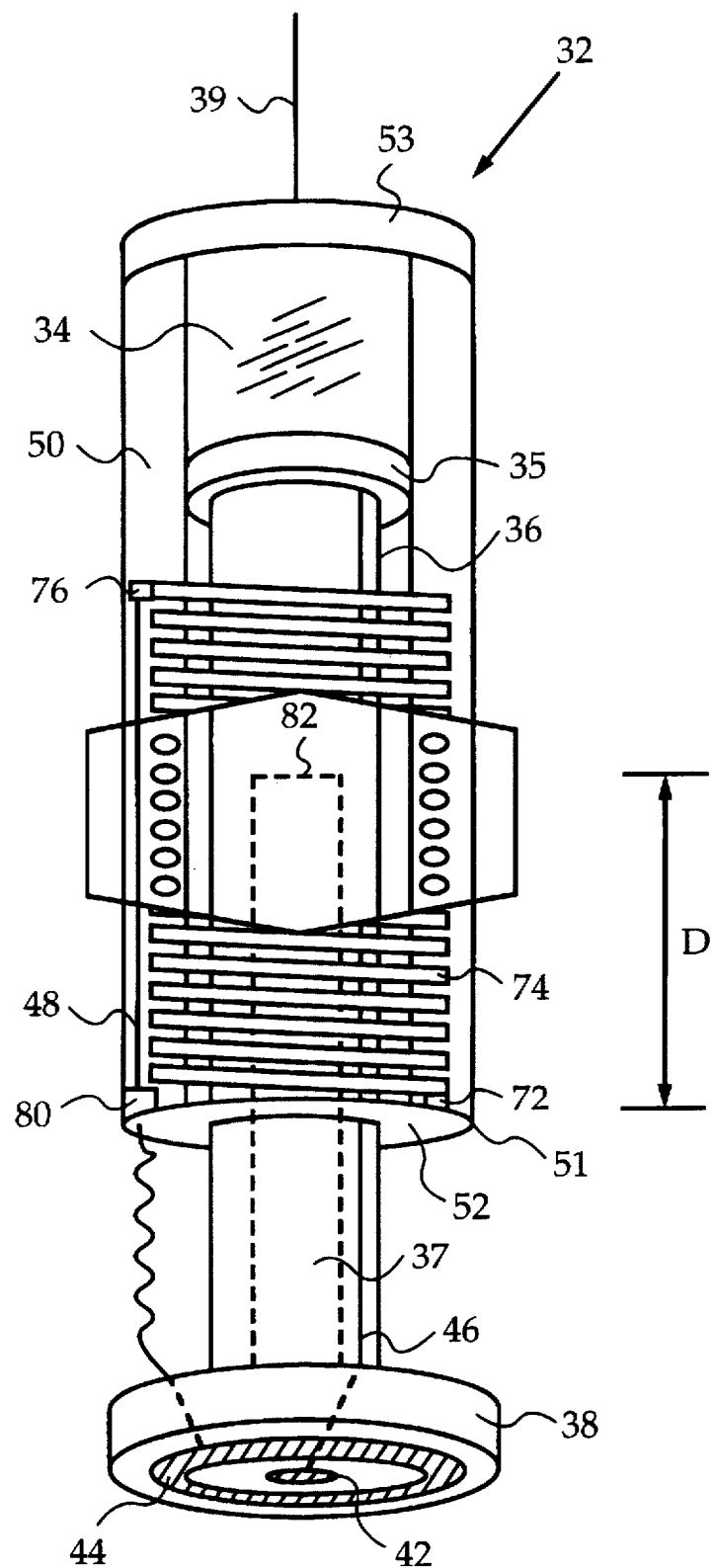
FIG. 2 is a three dimensional, schematic view and partial cross sectional view of a syringe according to the invention.
Figure 3:
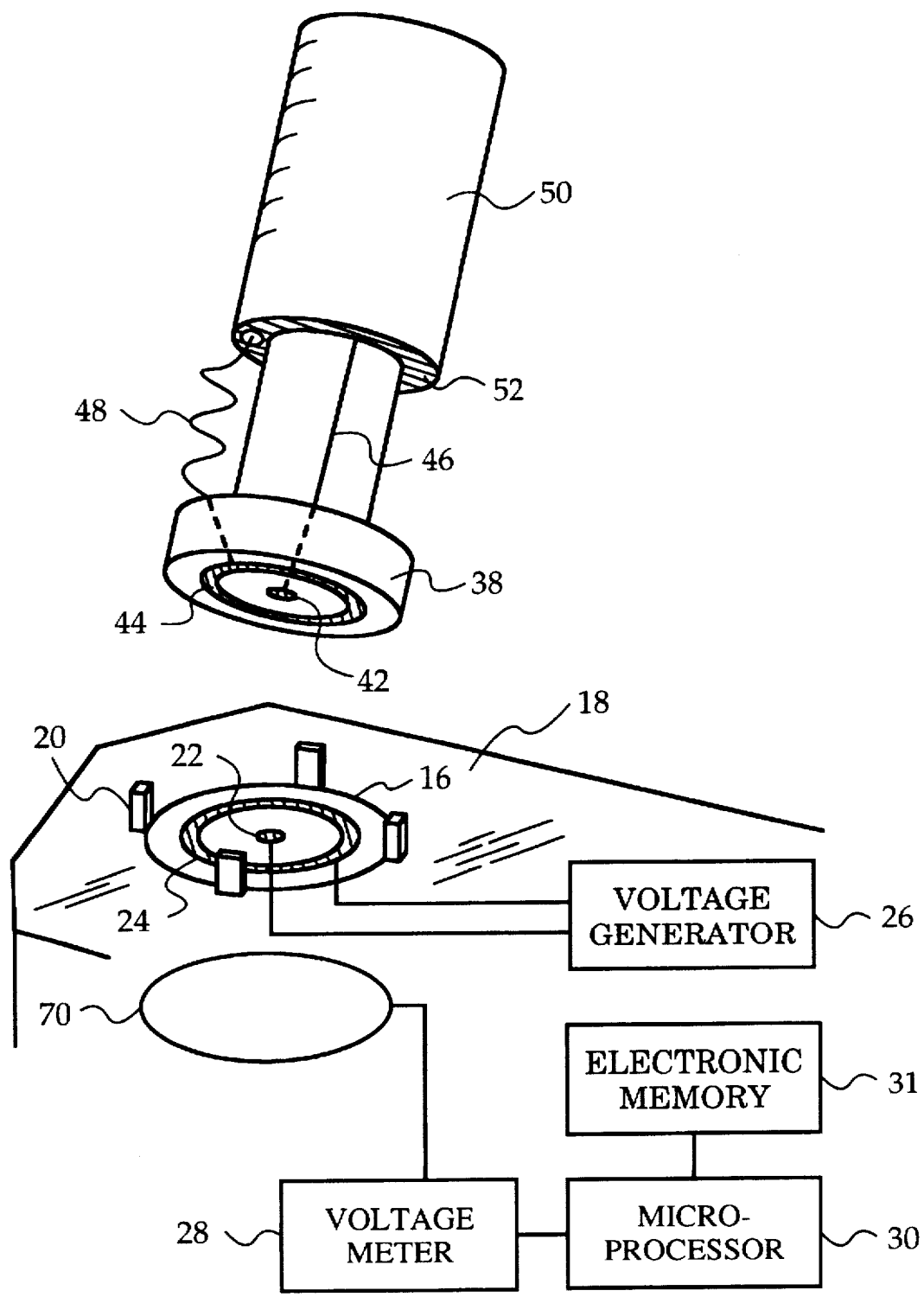
FIG. 3 is a perspective view and a partial block diagram of the syringe of FIG. 2 being placed on the apparatus of FIG. 1 for dose measurement.

A preferred embodiment of the invention is illustrated in FIGS. 1–3. Referring to FIG. 2, a syringe 32 has a barrel 50 for holding an agent 34. Barrel 50 has an insertion end 51 and an injection end 53. A plunger 36 having a piston section 35, a plunger rod 37, and a cap 38 is inserted through insertion end 51. A needle 39 is attached to injection end 53 such that needle 39 is in fluid communication with barrel 50. Plunger 36 is movably positioned in barrel 50 for expelling a dose of agent 34 through needle 39. Agent 34 occupies the inner volume of barrel 50 between piston section 35 and injection end 53.

Cap 38 has an input terminal 42 and an output terminal 44. Terminals 42 and 44 are made of an electrically conductive material, preferably copper. One end of a conducting strip 46 is attached to terminal 42. Conducting strip 46 extends from terminal 42 through cap 38 and along the outer surface of rod 37 parallel to the longitudinal axis of rod 37. Strip 46 terminates in a second end at piston section 35.

Barrel 50 has a rim 52 at insertion end 51. Rim 52 is lined with an electrically conductive material, preferably copper. Some of the electrically conductive material wraps inside barrel 50 to ensure rim 52 is in electrical contact with strip 46. Rim 52 is electrically connected to a first terminal 72 of an inductor 74 such that input terminal 42 is electrically connected to first terminal 72 through strip 46 and rim 52.

One end of inductor 74 is located at insertion end 51. Inductor 74 extends inside the walls of barrel 50 along two thirds of the length of barrel 50. At its other end, inductor 74 has a second terminal 76 One end of a connecting line 48 is connected to second terminal 76. The other end of connecting line 78 is routed through the wall of barrel 50, the space between barrel 50 and cap 38, and through cap 38 to output terminal 44. At rim 52, line 48 is insulated with an insulation sleeve 80 to prevent electrical contact with the conductive material lining rim 52.

A magnetically responsive core 82 is embedded concentrically inside plunger rod 37. Core 82 is cylindrical and has a length equal to two thirds of the length of barrel 50. Core 82 is positioned in rod 37 so that the ends of core 82 are aligned with the ends of inductor 74 when plunger 36 is fully inserted into barrel 50. As shown in FIG. 2, core 82 is inserted in inductor 74 a distance D that varies in dependence upon the position of plunger 36 inside barrel 50. Core 82 is made of a diamagnetic or paramagnetic material, or contains such material in its bulk, such that core 82 acts as magnetically responsive element within inductor 74. In the preferred embodiment, core 82 is made of iron shavings.

Referring to FIG. 1, an apparatus 10 has a housing 11 for holding the components of apparatus 10. Housing 11 is sufficiently compact to allow apparatus 10 to be hand-held and carried by a user. The top surface of housing 11 has a face plate 18. A circular placement field 16 is delineated on face plate 18. Placement field 16 is bordered on four sides by rigid positioning studs 20. Placement field 16 includes a circular input contact 22 positioned at the center of field 16 and a ring-shaped output contact 24 positioned concentrically to input contact 22. Both input contact 22 and output contact 24 are made of an electrically conductive material, preferably copper.

Below face plate 18 a voltage generator 26 is connected to contacts 22 and 24 such that voltage generator 26 produces a voltage difference V across input contact 22 and output contact 24. A voltage meter 28 is also located below face plate 18. Meter 28 is for measuring a magnetically induced voltage $\epsilon$, as will be explained in the operation section below. In the preferred embodiment, meter 28 is of the type that produces a digital measurement of voltage $\epsilon$. In an alternative embodiment, meter 28 is of the type that produces an analog measurement of voltage $\epsilon$. In this alternative embodiment, meter 28 is connected to an analog to digital converter (not shown) that converts the analog measurement into a digital measurement.

A microprocessor 30 is connected to meter 28 such that microprocessor 30 receives the digital measurement of voltage $\epsilon$ from meter 28. Microprocessor 30 is programmed to calculate the dose of agent 34 in barrel 50 from the measurement of voltage $\epsilon$, as will be explained in the operation section below. An electronic memory 31 is connected to microprocessor 30 such that memory 31 records the dose calculated by microprocessor 30. In the preferred embodiment, memory 31 is a digital memory unit.

Apparatus 10 further includes a testing device 12. Device 12 is of the type that tests a physical condition of a user and produces a digital value representative of the physical condition. Device 12 is connected to memory 31 such that memory 31 records the digital value representative of the physical condition. In the preferred embodiment, device 12 is a blood glucose meter and the digital value represents the user's blood glucose level.

A display 14 is recessed in face plate 18 and connected to memory 31 through microprocessor 30. Display 14 is for displaying to the user recorded data stored in memory 31. An input/output port 15 is located on the outer surface of housing 11. Port 15 is connected to memory 31 through microprocessor 30 such that recorded data in memory 31 may be transmitted through port 15 to a host computer 71 through a data connection cord 67.

FIG. 3 illustrates in detail the positioning of cap 38 on field 16 for dose measurement. Field 16 is designed for receiving cap 38 such that input terminal 42 contacts input contact 22 and output terminal 44 contacts output contact 24. Input terminal 42 is circular and positioned at the center of the outer surface of cap 38. Output terminal 44 is ring-shaped and positioned concentrically to input terminal 42 on the outer surface of cap 38. Terminal 42 has the same shape and dimensions as contact 22 and terminal 44 has the same shape and dimensions as contact 24. Positioning studs 20 are located around field 16 for aligning cap 38 on field 16. Studs 20 are positioned such that when cap 38 is placed on field 16 within positioning studs 20, terminals 42 and 44 establish electrical contact with contacts 22 and 24, respectively.

A conducting loop 70 is located below placement field 16 such that the centers of loop 70 and field 16 are vertically aligned. Loop 70 is made of an electrically conductive material such that a magnetic field produced by inductor 74 produces magnetically induced voltage $\epsilon$ in loop 70. In this embodiment, the diameter of loop 70 is equal to the diameter of field 16. In alternative embodiments, loop 70 is larger than field 16. Voltage meter 28 is connected to loop 70 such that voltage meter 28 measures magnetically induced voltage $\epsilon$ in loop 70.

The operation of the preferred embodiment is illustrated in FIGS. 1-3. To determine a blood glucose level, the user places a finger on device 12. Device 12 draws blood from the user's finger, tests the blood, and produces the digital value representative of the user's blood glucose level. This value is recorded in memory 31 and displayed on display 14 as a "blood glucose level" measurement. The user can now use this measurement to determine an appropriate dose of agent 34 to inject.

Before injecting the dose, the user first presses the outer surface of cap 38 against field 16. When cap 38 is properly pressed between positioning studs 20, input contact 22 and output contact 24 establish electrical contact with input terminal 42 and output terminal 44, respectively. Meanwhile, voltage generator 26 applies voltage difference V across input contact 22 and output contact 24. Voltage difference V causes an electric current I to flow through inductor 74. Current I produces a changing magnetic field B inside inductor 74 and along its axis. In particular, changing magnetic field B passes through measuring loop 70.

The intensity of magnetic field B passing through loop 70 is described by a magnetic flux $\psi$. Flux 9 is equal to the area of loop 70 times B. Changing magnetic field B results in changing flux $\psi$, which, in turn, induces voltage $\epsilon$ in loop 70 according to the well-known equation $\epsilon = d\psi/dt$. Magnetically active core 82 changes the intensity of magnetic field B depending on distance D that core 82 is inserted in inductor 74. As plunger 36 advances inside barrel 50 and a larger portion of core 82 is inserted inside inductor 74, the rate of change of flux dψ/dt changes as well.

Based on the above equation, this alters magnetically induced voltage ε in loop 70, so that the position of plunger 36 inside barrel 50 may be determined by a measurement of induced voltage ε. Because agent 34 occupies the inner volume of barrel 50 between piston 35 and injection end 53, the length of plunger 36 inside barrel 50 defines the dose of agent 34 in barrel 50. Thus, a measurement of induced voltage ε indicates the dose of agent 34 in barrel 50.

The measurement of induced voltage ε is performed by meter 28 and received by microprocessor 30. Microprocessor 30 calculates the dose of agent 34 from the measurement of induced voltage ε and records the dose in memory 31. Display 14 also displays the calculated dose as a "dose selected" measurement. This alerts the user that the injection of agent 34 can now be performed. After recording a desired number of doses, the user transmits the dose records recorded in memory 31 through port 15 to host computer 71.

In the preferred embodiment, microprocessor 30 is programmed during the manufacture of apparatus 10 with a table of values for performing the dosage calculation. The table includes a range of possible values of induced voltage ε, and a corresponding dose volume for each value of induced voltage ε. Upon receiving a voltage measurement, microprocessor 30 retrieves the dose volume corresponding to the voltage measurement from the table. The table of values is created by measuring induced voltage ε with meter 28 for various known volumes of agent 34 in barrel 50. The measured voltage for each known volume is then placed in the table. To create a precise table, at least ten known volumes of agent 34 ranging from a full barrel to an empty barrel should be measured to determine the corresponding induced voltage ε in loop 70.

Of course, many other methods of calculating dose information from measurements of induced voltage ε are possible. For example, in one alternative embodiment, microprocessor 30 is programmed to calculate doses using a mathematical function derived from the table of values described in the preferred embodiment. Using the known volumes of agent 34 and the corresponding voltage measurements produced by meter 28, a graph of dose volume as a function of measured voltage is created. By interpolating from the known points on the graph, a mathematical function is derived describing the relationship of measured voltage to dose volume. Microprocessor 30 then uses the derived mathematical function to calculate dose volumes from the measured voltages. Specific techniques for calibrating an electronic apparatus by interpolating from test measurements are well known in the art.

The advantage of the apparatus described in the preferred embodiment is that it electrically measures doses directly from an injection syringe and digitally records the dose measurements. The user is not burdened with manually entering the dose information into a log. Additionally, the dose information recorded is more accurate than a user's manual records, which have been shown to be unreliable.

Figure 4:
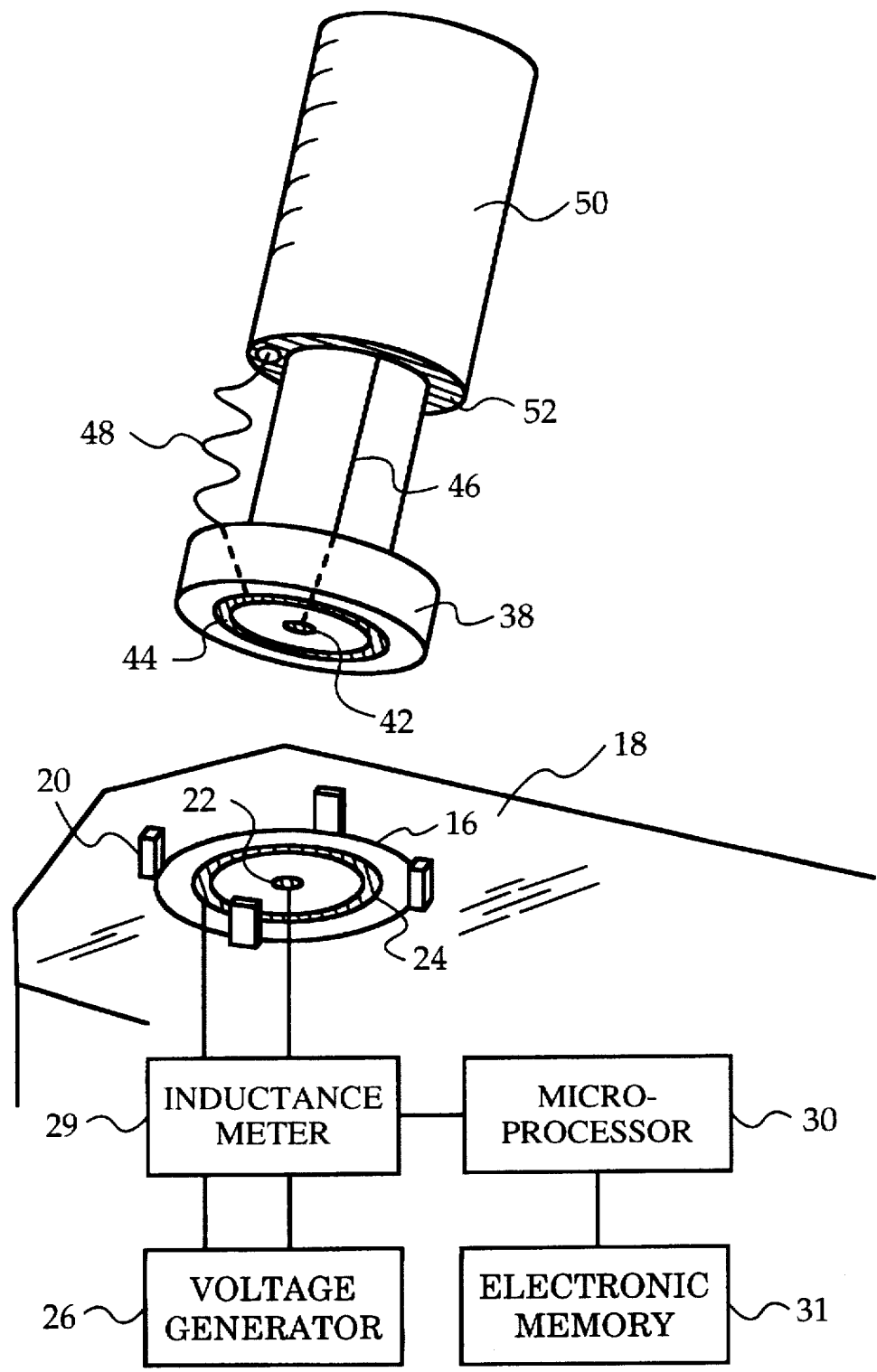
FIG. 4 is a perspective view and a partial block diagram of the syringe of FIG. 2 being placed on another apparatus according to the invention.

A second embodiment of the invention is shown in FIG. 4. The second embodiment differs from the preferred embodiment in that apparatus 10 is designed to measure an inductance L of inductor 74 rather than a magnetic field generated by inductor 74. Inductance L also varies in dependence upon the portion of core 82, and hence plunger 36, inside barrel 50, so that the dose of agent 34 contained in barrel 50 may be determined by a measurement of inductance L.

Referring to FIG. 4, loop 70 and meter 28 are replaced by an inductance meter 29 located below face plate 18. Meter 29 is connected to contacts 22 and 24 to measure inductance L.

Microprocessor 30 is connected to meter 29 such that microprocessor 30 receives the measurements of inductance L from meter 29. Meter 29 is preferably of the type that produces a digital measurement of inductance L. Alternatively, meter 29 is of the type that produces an analog measurement of inductance L. In this alternative embodiment, meter 29 is connected to an analog to digital converter (not shown) that converts the analog measurement into a digital measurement. Voltage generator 26 is connected to contacts 22 and 24 through meter 29 such that voltage generator 26 applies voltage difference V across input contact 22 and output contact 24 through meter 29.

The operation of the second embodiment is similar to the operation of the preferred embodiment. The primary difference is that apparatus 10 measures inductance L rather than induced voltage ε when electric current I flows through inductor 74. Microprocessor 30 is programmed to calculate doses from the inductance measurements of meter 29 in the same manner it is programmed to calculate doses from voltage measurements in the preferred embodiment. Other than the differences described, the operation and advantages of this second embodiment are the same as those described in the preferred embodiment above.

Figure 5:
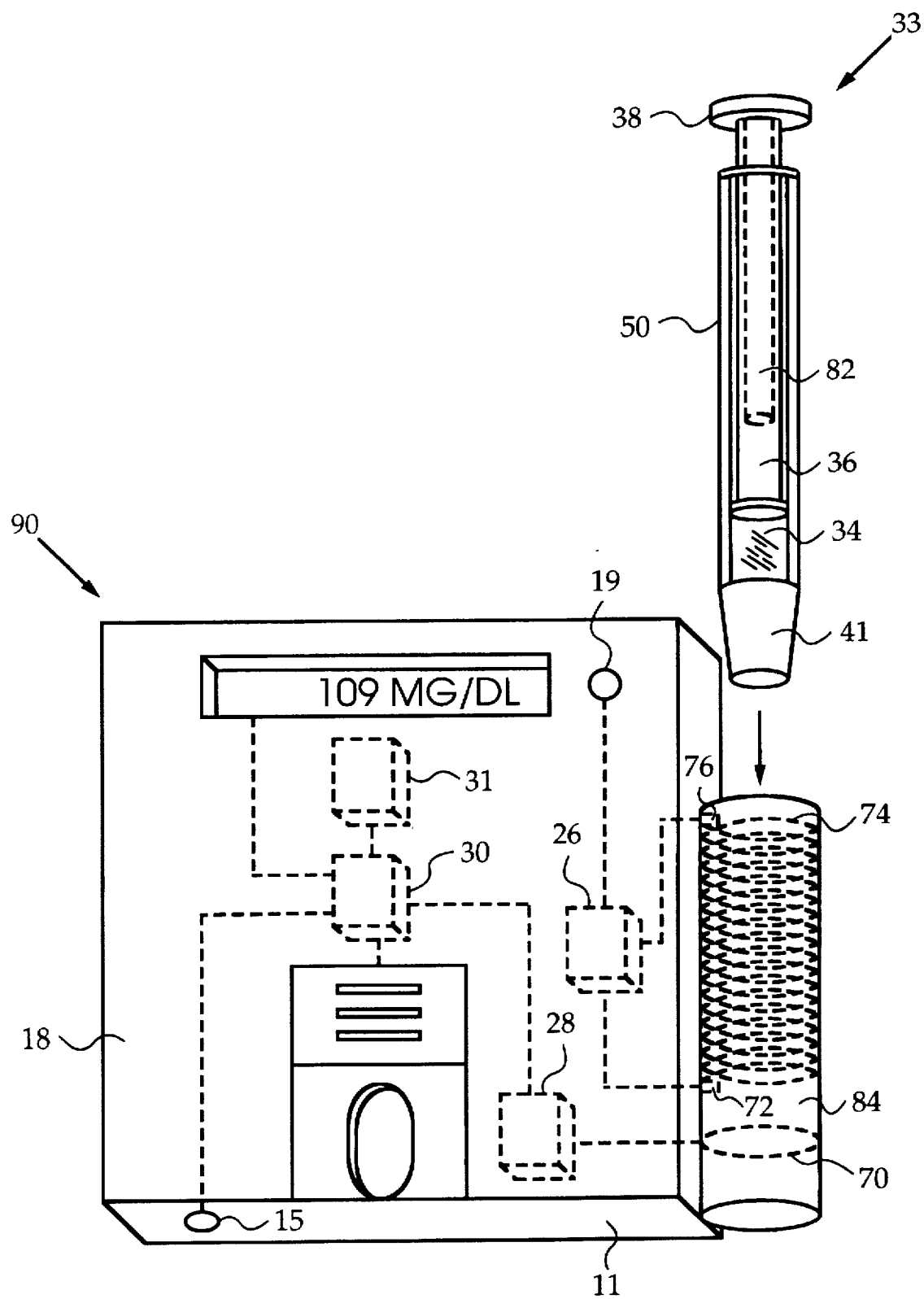
FIG. 5 is a three dimensional, schematic view of another syringe being placed into another apparatus for dose measurement.

A third embodiment of the invention is shown in FIG. 5. The third embodiment differs from the preferred embodiment in that inductor 74 is located within the apparatus rather than within the syringe. Referring to FIG. 5, a syringe 33 is similar to the syringe described in the preferred embodiment in that it has barrel 50 for holding agent 34, plunger 36 for expelling agent 34, and core 82 embedded in plunger 36. However, inductor 74, strip 46, line 48, rim 52, input terminal 42, and output terminal 44 are eliminated from syringe 33, simplifying its manufacture. Syringe 33 also includes a syringe cap 41 for covering needle 39.

An apparatus 90 has similar parts to those described for the apparatus of the preferred embodiment except that housing 11 now has a receptacle 84 located on its side surface. Receptacle 84 is made of a non-electrically conductive material and is designed for receiving syringe 33 for dose measurement. In this embodiment, syringe 33 is placed in receptacle 84 by inserting the end of syringe 33 having cap 41. Of course, in alternative embodiments, syringe 33 may be placed in receptacle 84 by inserting the end of syringe 33 having cap 38. Also in this embodiment, syringe 33 is essentially cylindrical in shape, so that receptacle 84 is also cylindrical. Of course, in alternative embodiments, receptacle 84 may be designed to receive syringes of different shapes and sizes.

Inductor 74 is positioned coaxially to receptacle 84, preferably by embedding inductor 74 in the walls of receptacle 84. Alternatively, inductor 74 may be mounted to the inner surface of receptacle 84. Inductor 74 is further positioned in receptacle 84 such that when syringe 33 is placed in receptacle 84 with plunger 36 fully inserted in barrel 50, the ends of core 82 are aligned with the ends of inductor 74.

Voltage generator 26 is connected to terminals 72 and 76 to produce voltage difference V across inductor 74, thereby causing electric current I to flow through inductor 74. A button 19 for controlling voltage generator 26 is located on face plate 18. Button 19 is connected to voltage generator 26 such that voltage generator 26 applies voltage V when button 19 is depressed. Conducting loop 70 is positioned coaxially to receptacle 84, preferably by embedding loop 70 in the walls of receptacle 84 below inductor 74. Alternatively, loop 70 may be attached to the inner surface of receptacle 84. Voltage meter 28 is connected to loop 70 such that voltage meter 28 measures magnetically induced voltage ε in loop 70.

The operation of the third embodiment is shown in FIG. 5. Before injecting the dose, the user places syringe 33 in receptacle 84 by inserting the end of syringe 33 having cap 41. The user then presses button 19 to cause voltage generator 26 to produce voltage difference V across inductor 74. Voltage difference V causes electric current I to flow through inductor 74. Current I generates changing magnetic field B inside inductor 74, which produces induced voltage ε in loop 70.

The remaining operation of the third embodiment is similar to the operation of the preferred embodiment. Microprocessor 30 is programmed to calculate doses from the measurements of induced voltage ε in the same manner as that described in the preferred embodiment. The advantage of the third embodiment is the simplification of syringe 33. Because the syringe does not require an inductor or electrical wires, it may be manufactured and used with greater ease.

Figure 6:
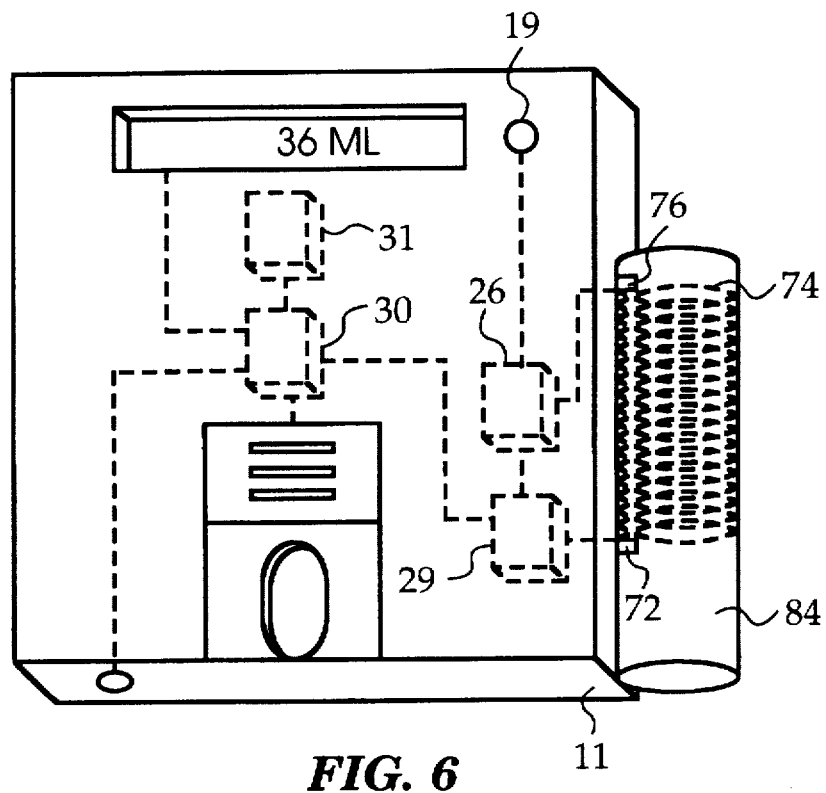
FIG. 6 is a three dimensional, schematic view of another apparatus according to the invention.

A fourth embodiment of the invention is shown in FIG. 6. The fourth embodiment differs from the third embodiment in that apparatus 10 is designed to measure inductance L of inductor 74 rather than the intensity of a magnetic field generated by inductor 74. Referring to FIG. 6, loop 70 and meter 28 are replaced by inductance meter 29 located below face plate 18. Meter 29 is connected to terminals 72 and 76 to measure inductance L. Microprocessor 30 is connected to meter 29 such that microprocessor 30 receives the measurements of inductance L from meter 29. Voltage generator 26 is connected to terminals 72 and 76 through meter 29 such that voltage generator 26 applies voltage difference V across terminals 72 and 76 through meter 29.

The operation of the fourth embodiment is similar to the operation of the third embodiment. The primary difference is that apparatus 10 measures inductance L rather than induced voltage ε when electric current I flows through inductor 74. Microprocessor 30 is programmed to calculate doses from the inductance measurements of meter 29 in the same manner it is programmed to calculate doses from voltage measurements in the preferred embodiment. Other than the differences described, the operation and advantages of this fourth embodiment are the same as those described in the third embodiment above.

Figure 7:
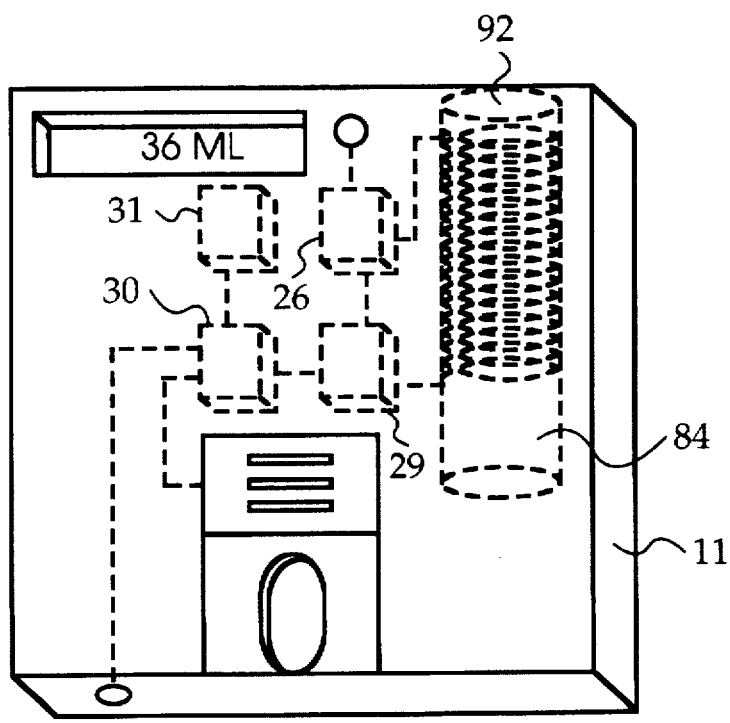
FIG. 7 is a three dimensional, schematic view of another apparatus according to the invention.

FIG. 7 illustrates an alternative location for receptacle 84. Receptacle 84 is located within housing 11 rather than at the side surface of housing 11. Housing 11 has an opening 92 for placement of syringe 33 in receptacle 84. One advantage of locating receptacle 84 within housing 11 is that apparatus 10 is rendered more compact for easier carrying and storing of apparatus 10. Another advantage is that receptacle 84 is insulated so that it is less prone to fracture.

SUMMARY, RAMIFICATIONS, AND SCOPE

Although the above description includes many specificities, these should not be construed as limitations on the scope of the invention, but merely as illustrations of some of the presently preferred embodiments. Many other embodiments of the invention are possible. For example, in one alternative embodiment, the microprocessor is eliminated from the apparatus so that the induced voltage measurements are recorded directly into the electronic memory. In this embodiment, the host computer is programmed to calculate the doses from the received voltage measurements in the same manner as the microprocessor of the preferred embodiment.

Additionally, the placement field may have shapes differing from the circular shape described. The placement field could be square, hexagonal, or any other shape that aids a user in placing a syringe on the apparatus. Additionally, the placement field could be recessed in the face plate so that the positioning studs are unnecessary. Similarly, the input terminal and output terminal need not be located on the plunger cap. They could be located on the outside of the barrel or any other place that aids a user in contacting the terminals to the apparatus for dose measurement.

Furthermore, the apparatus is not limited to measuring and recording doses from only one size syringe. In another embodiment, the apparatus includes a microprocessor which is programmed to calculate doses from syringes of different sizes. The microprocessor is connected to a user interface through which the user enters the size of the syringe he or she is using. Moreover, the apparatus is not limited to aiding a self-care diabetes program. It may be used to aid in the administration of any program that requires injections.

Therefore, the scope of the invention should be determined not by the examples given but by the appended claims and their legal equivalents.

We claim:

1. In combination with a syringe, an apparatus for determining and recording a dose of an agent delivered with said syringe, said syringe being of the type comprising:

a) a barrel for holding said agent;

b) a plunger movably positioned in said barrel for expelling said agent, said plunger comprising a magnetically responsive element selected from the group consisting of diamagnetic materials and paramagnetic materials;

c) an inductive element for generating a magnetic field, said inductive element being coupled to said barrel such that the intensity of said magnetic field varies in dependence upon the position of said plunger in said barrel, and said inductive element having a first terminal and a second terminal;

d) an input terminal located on the outside of said syringe and electrically connected to said first terminal;

e) an output terminal located on the outside of said syringe and electrically connected to said second terminal;

said apparatus comprising:

a) a housing;

b) a field on the outside of said housing, said field having an input contact for contacting said input terminal and an output contact for contacting said output terminal;

c) a voltage generating means for producing a voltage difference across said input contact and said output contact, thereby causing an electric current to flow through said inductive element when said input contact is contacting said input terminal and said output contact is contacting said output terminal;

d) a magnetic response measuring means located within said housing for measuring said magnetic field and for calculating from the measurement of said magnetic field said dose; and e) a recording means connected to said magnetic response measuring means for recording said dose.

2. The combination syringe and apparatus of claim 1, further comprising an input/output port located on a surface of said housing and connected to said recording means for transmitting recorded data from said recording means to a host computer.

3. The combination syringe and apparatus of claim 1, further comprising a testing means for testing a physical condition of a user and for producing a digital value representative of said physical condition, said testing means being connected to said recording means such that said recording means records said digital value representative of said physical condition.

4. The combination syringe and apparatus of claim 1, further comprising a display recessed in said housing and connected to said recording means for displaying recorded data.

5. The combination syringe and apparatus of claim 1, wherein said input terminal and said output terminal are located on a cap of said plunger.

6. The combination syringe and apparatus of claim 5, wherein said input terminal is circular and positioned at the center of said cap and wherein said output terminal is ring-shaped and positioned concentrically to said input terminal.

7. The combination syringe and apparatus of claim 5, wherein said input contact is circular and positioned at the center of said field and wherein said output contact is ring-shaped and positioned concentrically to said input contact.

8. The combination syringe and apparatus of claim 5, wherein said field is bordered by a positioning means for aligning said cap on said field such that when said cap is placed within said positioning means, said input terminal contacts said input contact and said output terminal contacts said output contact.

9. The combination syringe and apparatus of claim 1, wherein said magnetic response measuring means comprises a voltage meter connected to a conducting loop such that said voltage meter measures a magnetically induced voltage in said conducting loop.

10. The combination syringe and apparatus of claim 1, wherein said recording means comprise a digital memory unit.

11. The combination syringe and apparatus of claim 1, wherein said housing is sufficiently compact to enable said apparatus to be hand-held and carried by a user.

12. In combination with a syringe, an apparatus for determining and recording a dose of an agent delivered with said syringe, said syringe being of the type comprising:
 a) a barrel for holding said agent;
 b) a plunger movably positioned in said barrel for expelling said agent, said plunger comprising a magnetically responsive element selected from the group consisting of diamagnetic materials and paramagnetic materials;
 c) an inductive element coupled to said barrel such that the inductance of said inductive element varies in dependence upon the position of said plunger in said barrel, said inductive element having a first terminal and a second terminal;
 d) an input terminal located on the outside of said syringe and electrically connected to said first terminal;
 e) an output terminal located on the outside of said syringe and electrically connected to said second terminal;
said apparatus comprising:
 a) a housing;
 b) a field on the outside of said housing, said field having an input contact for contacting said input terminal and an output contact for contacting said output terminal;
 c) a voltage generating means for producing a voltage difference across said input contact and said output contact, thereby causing an electric current to flow through said inductive element when said input contact is contacting said input terminal and said output contact is contacting said output terminal;
 d) an inductance measuring means located within said housing for measuring the inductance of said inductive element and for calculating from the inductance said dose; and
 e) a recording means connected to said inductance measuring means for recording said dose.

13. The combination syringe and apparatus of claim 12, further comprising an input/output port located on a surface of said housing and connected to said recording means for transmitting recorded data from said recording means to a host computer.

14. The combination syringe and apparatus of claim 12, further comprising a testing means for testing a physical condition of a user and for producing a digital value representative of said physical condition, said testing means being connected to said recording means such that said recording means records said digital value representative of said physical condition.

15. The combination syringe and apparatus of claim 12, further comprising a display recessed in said housing and connected to said recording means for displaying recorded data.

16. The combination syringe and apparatus of claim 12, wherein said input terminal and said output terminal are located on a cap of said plunger.

17. The combination syringe and apparatus of claim 16, wherein said input terminal is circular and positioned at the center of said cap and wherein said output terminal is ring-shaped and positioned concentrically to said input terminal.

18. The combination syringe and apparatus of claim 16, wherein said input contact is circular and positioned at the center of said field and wherein said output contact is ring-shaped and positioned concentrically to said input contact.

19. The combination syringe and apparatus of claim 16, wherein said field is bordered by a positioning means for aligning said cap on said field such that when said cap is placed within said positioning means, said input terminal contacts said input contact and said output terminal contacts said output contact.

20. The combination syringe and apparatus of claim 12, wherein said inductance measuring means comprises an inductance meter connected to said input contact and said output contact such that said inductance meter measures the inductance of said inductive element when said electric current flows through said inductive element.

21. The combination syringe and apparatus of claim 12, wherein said recording means comprise a digital memory unit.

22. The combination syringe and apparatus of claim 12, wherein said housing is sufficiently compact to enable said apparatus to be hand-held and carried by a user.

23. In combination with a syringe, an apparatus for determining and recording a dose of an agent delivered with said syringe, said syringe being of the type comprising:
 a) a barrel for holding said agent;
 b) a plunger movably positioned in said barrel for expelling said agent, said plunger comprising a magnetically responsive element selected from the group consisting of diamagnetic materials and paramagnetic materials;
said apparatus comprising:
 a) a housing having a receptacle for receiving said syringe;

b) an inductive element for generating a magnetic field, said inductive element having a first terminal and a second terminal, and said inductive element being positioned coaxially to said receptacle such that when said syringe is placed in said receptacle, the intensity of said magnetic field varies in dependence upon the position of said plunger in said barrel;

c) a voltage generating means for producing a voltage difference across said first terminal and said second terminal, thereby causing an electric current to flow through said inductive element;

d) a magnetic response measuring means for measuring said magnetic field and for calculating from the measurement of said magnetic field said dose; and e) a recording means connected to said magnetic response measuring means for recording said dose.

24. The combination syringe and apparatus of claim 23, further comprising an input/output port connected to said recording means for transmitting recorded data from said recording means to a host computer.

25. The combination syringe and apparatus of claim 23, further comprising a testing means for testing a physical condition of a user and for producing a digital value representative of said physical condition, said testing means being connected to said recording means such that said recording means records said digital value representative of said physical condition.

26. The combination syringe and apparatus of claim 23, further comprising a display connected to said recording means for displaying recorded data.

27. The combination syringe and apparatus of claim 23, wherein said magnetic response measuring means comprises a voltage meter connected to a conducting loop such that said voltage meter measures a magnetically induced voltage in said conducting loop.

28. In combination with a syringe, an apparatus for determining and recording a dose of an agent delivered with said syringe, said syringe being of the type comprising:

a) a barrel for holding said agent;

b) a plunger movably positioned in said barrel for expelling said agent, said plunger comprising a magnetically responsive element selected from the group consisting of diamagnetic materials and paramagnetic materials;

said apparatus comprising:

a) a housing having a receptacle for receiving said syringe;

b) an inductive element having a first terminal and a second terminal, said inductive element being positioned coaxially to said receptacle such that when said syringe is placed in said receptacle, the inductance of said inductive element varies in dependence upon the position of said plunger in said barrel;

c) a voltage generating means for producing a voltage difference across said first terminal and said second terminal, thereby causing an electric current to flow through said inductive element;

d) an inductance measuring means for measuring the inductance of said inductive element and for calculating from the inductance said dose; and e) a recording means connected to said magnetic response measuring means for recording said dose.

29. The combination syringe and apparatus of claim 28, further comprising an input/output port connected to said recording means for transmitting recorded data from said recording means to a host computer.

30. The combination syringe and apparatus of claim 28, further comprising a testing means for testing a physical condition of a user and for producing a digital value representative of said physical condition, said testing means being connected to said recording means such that said recording means records said digital value representative of said physical condition.

31. The combination syringe and apparatus of claim 28, further comprising a display connected to said recording means for displaying recorded data.

32. The combination syringe and apparatus of claim 28, wherein said inductance measuring means comprises an inductance meter connected to said input contact and said output contact such that said inductance meter measures the inductance of said inductive element when said electric current flows through said inductive element.

* * * * *